United States Patent
Bertolini et al.

(10) Patent No.: US 9,410,169 B2
(45) Date of Patent: Aug. 9, 2016

(54) PROCESS FOR PRODUCING CHIRAL 1-SUBSTITUTED 2-PIPERIDINOLS EMPLOYING OXIDOREDUCTASES

(75) Inventors: Giorgio Bertolini, Segrate (IT); Paolo Magri', Mendrisio (CH)

(73) Assignee: LABORATORIO CHIMICO INTERNAZIONALE S.P.A., Milan (IT)

( * ) Notice: Subject to any disclaimer, the term of this patent is extended or adjusted under 35 U.S.C. 154(b) by 0 days.

(21) Appl. No.: 14/406,924

(22) PCT Filed: Jun. 18, 2012

(86) PCT No.: PCT/IB2012/001178
§ 371 (c)(1),
(2), (4) Date: Apr. 8, 2015

(87) PCT Pub. No.: WO2013/190341
PCT Pub. Date: Dec. 27, 2013

(65) Prior Publication Data
US 2015/0275249 A1 Oct. 1, 2015

(51) Int. Cl.
*C12P 13/00* (2006.01)
*C12P 17/12* (2006.01)
*C12N 9/02* (2006.01)
*C12N 9/04* (2006.01)
*C07D 211/42* (2006.01)

(52) U.S. Cl.
CPC ............... *C12P 17/12* (2013.01); *C07D 211/42* (2013.01); *C12N 9/0008* (2013.01); *Y02P 20/52* (2015.11)

(58) Field of Classification Search
CPC ...... C12P 13/001; C12P 13/008; C12P 17/12; C12N 9/0008
USPC .................................................. 435/122, 189
See application file for complete search history.

(56) References Cited

FOREIGN PATENT DOCUMENTS

WO WO 2004/111083 12/2004
WO WO 2009/040080 4/2009

OTHER PUBLICATIONS

International Search Report for PCT/IB2012/001178 mailed Jul. 1, 2013.
Written Opinion of the International Searching Authority for PCT/IB2012/001178 mailed Jul. 1, 2013.
R. Lacheretz et al., "Daucus Carota Mediated-Reduction of Cyclic 3-Oxo-amines", Organic Letters, vol. 11, No. 6, 2009, pp. 1245-1248.
J.J. Van Luppen et al., "Enzymatic in Vitro Reduction of Ketones, Part 13. HLAD-Catalyzed Reduction of 3-Piperidone Derivatives to Piperidinols with High Enantiomeric Purity", Studies in Organic Chemistry, (Bio-Organic Heterocycles), vol. 18, 1984, pp. 277-280.
N. Kizaki et al., "Characterization of Novel Alcohol Dehydrogenase of Devosia Riboflavina Involved in Stereoselective Reduction of 3-Pyrrolidinone Derivatives", Journal of Molecular Catalysis, vol. 51, No. 3-4, Nov. 9, 2007, pp. 73-80.
International Preliminary Report on Patentability for PCT/IB2012/001178, mailed Jun. 26, 2014, 17 pages.

*Primary Examiner* — Younus Meah
(74) *Attorney, Agent, or Firm* — Nixon & Vanderhye P.C.

(57) ABSTRACT

The present invention relates to an enantioselective enzymatic process for the preparation of an optically active 3-hydroxypiperidinecarboxylic acid derivative.

8 Claims, No Drawings

PROCESS FOR PRODUCING CHIRAL 1-SUBSTITUTED 2-PIPERIDINOLS EMPLOYING OXIDOREDUCTASES

This application is the U.S. national phase of International Application No. PCT/IB2012/00117818 filed 18 Jun. 2012, which designated the U.S., the entire contents of which is hereby incorporated by reference.

SEQUENCE LISTING

The instant application contains a Sequence Listing which has been submitted electronically in ASCII format and is hereby incorporated by reference in its entirety. Said ASCII copy, created on Apr. 8, 2015, is named 367-354_SL.txt and is 40,357 bytes in size.

SUMMARY OF THE INVENTION

The present invention relates to an enantioselective enzymatic process for the preparation of an optically active 3-hydroxypiperidinecarboxylic acid derivative.

TECHNICAL BACKGROUND

Some optically active 3-hydroxypiperidinecarboxylate esters are useful intermediates in the synthesis of interesting pharmaceutical agents.

In general, optically active hydroxyl compounds may be obtained by resolution of the corresponding racemate by known chemical or enzymatic methods. These resolutions have many drawbacks such as, for instance, the yield of the desired enantiomer which of course cannot be more that 50% of the starting racemate compound.

OBJECTS OF THE INVENTION

It is one object of the present invention to provide a process for the preparation of an optically active 3-hydroxypiperidinecarboxylate derivative which is simple, safe and cost-effective.

Another object of the invention is to provide a process for the preparation of an optically active 3-hydroxypiperidinecarboxylate derivative by enzymatic reduction of the corresponding oxo-derivatives.

Another object of the invention is to provide enantiomerically pure optically active 3-hydroxypiperidinecarboxylic acid and its esters.

DESCRIPTION OF THE INVENTION

So, according to one of its aspects, the present invention relates to a process for the preparation of a compound of formula (I)

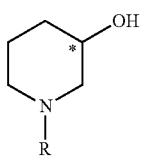

(I)

wherein the chiral carbon is in the (R) or in the (S) configuration;

R is selected from hydrogen and $COR_1$;

$R_1$ is selected from hydrogen, $C_1$-$C_6$-alkyl and $OR_2$;

$R_2$ is selected from $C_1$-$C_6$-alkyl, benzyl, said benzyl being optionally substituted by one or more $C_1$-$C_6$-alkyl groups;

which comprises reducing a compound of formula (II)

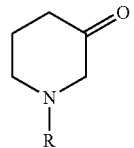

(II)

wherein R is defined as above, with an oxidoreductase enzyme, in the presence of a cofactor and of a cosubstrate regenerating said cofactor.

The compounds of formula (II), herein also "substrate", are known in the art.

According to the present invention, the term "alkyl" means a linear or branched, saturated or non-saturated alkyl group. According to a preferred embodiment of the invention, $C_1$-$C_6$-alkyl is tert-butyl.

According to a preferred embodiment of the invention, R is $COR_1$.

According to another preferred embodiment of the invention, $R_1$ is $OR_2$.

According to another preferred embodiment of the invention R is COOtBu or COObenzyl.

According to another preferred embodiment of the invention the compound of formula (I) is in the (S) configuration.

The oxidoreductase enzyme which is used in the process of the invention is preferably a polypeptide of yeast or bacterial origin.

According to an advantageous embodiment of the invention, the cofactor is selected from nicotineamide adenine dinucleotide phosphate (NADP) and nicotineamide adenine dinucleotide (NAD).

According to an advantageous embodiment of the invention the cosubstrate is a secondary alcohol, preferably a secondary alcohol selected from $C_1$-$C_{10}$—OH, such as 2-propanol, 2-butanol, 2-pentanol, 4-methyl-2-pentanol, 2-heptanol and 2-octanol, preferably 2-propanol or 4-methyl-2-pentanol, most preferably 2-propanol.

According to a most preferred embodiment of the invention, the oxidoreductase is selected from SEQ ID NO: 1, SEQ ID NO: 2, SEQ ID NO: 3 or SEQ ID NO:4, SEQ ID NO: 5, SEQ ID NO: 6, SEQ ID NO: 7, SEQ ID NO: 8 and SEQ ID NO:9.

The use of an oxidoreductase enzyme selected from SEQ ID NO: 1, SEQ ID NO: 2, SEQ ID NO: 3 or SEQ ID NO:4, SEQ ID NO: 5, SEQ ID NO: 6, SEQ ID NO: 7, SEQ ID NO: 8, SEQ ID NO:9 and derivatives thereof, such as an amino acid sequence having at least 60% identity with any one of said sequences, for the preparation of compound of formula (I) from compound of formula (II) constitutes another aspect of the present invention.

SEQ ID NO: 1 is a preferred oxidoreductase enzyme for the process of the invention.

According to a preferred aspect, the invention relates to a process for the preparation of a compound of formula (I')

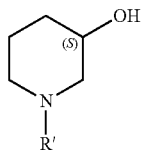

(I')

wherein the chiral carbon is in the (S)-configuration, and R' is selected from H, COOtBu or COObenzyl, which comprises reducing a compound of formula (II')

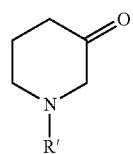

(II')

wherein R' is defined as above, with an oxidoreductase of SEQ ID NO: 1, in the presence of a cofactor and of a cosubstrate regenerating said cofactor.

The cofactor and the cosubstrate are preferably those indicated as preferred above.

So, according to a most preferred aspect, the invention relates to a process for the preparation of a compound of formula (I') by reduction of compound of formula (II') with an oxidoreductase of SEQ ID NO: 1, in the presence of NADH or NADPH as a cofactor and of a secondary alcohol, especially 2-propanol or 4-methyl-2-pentanol, most preferably 2-propanol, as a cosubstrate regenerating said cofactor.

According to a preferred embodiment, R' is COOtBu.

According to another of its aspects, the invention relates to a compound of formula (I') as defined above, containing less than 0.1% of the (R) isomer, preferably to a compound of formula (I') wherein R' is COOtBu.

The organism producing the oxidoreductase enzymes useful in the enantioselective enzymatic reduction may be a wild strain or a variant and is preferably selected from Yeast or bacteria, for instance, yeast of the *Candida* or *Pichia* genus.

The oxidoreductases of SEQ ID NO: 1 to SEQ ID NO: 9 are known in the art.

A polypeptide comprising SEQ ID NO:1 may be encoded by a DNA sequence which is obtainable, for example, from the organism *Pichia capsulata* or by a nucleic acid sequence that hybridizes therewith, disclosed in EP 1 633 779.

A polypeptide comprising SEQ ID NO:2 may be encoded by a DNA sequence which is obtainable, for example, from the organism *Rhodococcus erythropolis*, or by a nucleic acid sequence that hybridizes therewith, disclosed in EP 1499716.

A polypeptide comprising SEQ ID NO:3 may be encoded by a DNA sequence which is obtainable, for example, from the organism *Metschnikowia zobellii*, or by a nucleic acid sequence that hybridizes therewith, disclosed in EP 1685248.

A polypeptide comprising SEQ ID NO:4 may be encoded by a DNA sequence which is obtainable, for example, from the organism *Candida parapsilosis* or by a nucleic acid sequence that hybridizes therewith, disclosed in Enzyme Microb Technol. 1993 November; 15 (11):950-8.

A polypeptide comprising SEQ ID NO:5 may be encoded by a DNA sequence which is obtainable, for example, from the organism *Thermoanerobium brockii* or by a nucleic acid sequence that hybridizes therewith, disclosed in J. Am. Chem. Soc. 1986, 108, pages 162-

A polypeptide comprising SEQ ID NO:6 may be encoded by a DNA sequence which is obtainable, for example, from the organism *Microbacterium* sp or by a nucleic acid sequence that hybridizes therewith, disclosed in WO2007/012428

A polypeptide comprising SEQ ID NO:7 may be encoded by a DNA sequence which is obtainable, for example, from the organism *Rhodococcus ruber* or by a nucleic acid sequence that hybridizes therewith, disclosed in Angew Chem Int Ed Engl. 2002 march 15; 41 (6):1014.

A polypeptide comprising SEQ ID NO:8 may be encoded by a DNA sequence which is obtainable, for example, from the organism *Pichia stipidis* or by a nucleic acid sequence that hybridizes therewith, disclosed in WO2007/012428.

A polypeptide comprising SEQ ID NO:9 may be encoded by a DNA sequence which is obtainable, for example, from the organism *Gordonia rubripertincta* or by a nucleic acid sequence that hybridizes therewith, disclosed in WO2007/012428.

The DNA sequences may be any DNA coding for polypeptides (SEQ ID No:1, SEQ ID No:2, SEQ ID No:3, SEQ ID No:4, SEQ ID No:5, SEQ ID No:6, SEQ ID No:7, SEQ ID No:8, SEQ ID No:9). It may be a DNA having the nucleotide sequence shown under SEQ ID No:10, SEQ ID No:11, SEQ ID No:12, SEQ ID No:13, SEQ ID No:14, SEQ ID No:15, SEQ ID No:16, SEQ ID No:17, SEQ ID No:18 in the attached sequence listing, or the DNA coding for a polypeptides having enzyme activity in the asymmetric reduction of the invention, and hybridizing with the DNA having the nucleotide sequence shown under SEQ ID No:10, SEQ ID No:11, SEQ ID No:12, SEQ ID No:13, SEQ ID No:14, SEQ ID No:15, SEQ ID No:16, SEQ ID No:17, SEQ ID No:18 in the sequence listing under stringent conditions.

The term "DNA hybridizing with the DNA having the nucleotide sequence shown under SEQ ID No:10, SEQ ID No:11, SEQ ID No:12, SEQ ID No:13, SEQ ID No:14, SEQ ID No:15, SEQ ID No:16, SEQ ID No:17, SEQ ID No:18 in the sequence listing under stringent conditions" means a DNA obtainable by the technique of colony hybridization, plaque hybridization or southern hybridization, using the DNA having the nucleotide sequence shown under SEQ ID No:10, SEQ ID No:11, SEQ ID No:12, SEQ ID No:13, SEQ ID No:14, SEQ ID No:15, SEQ ID No:16, SEQ ID No:17, SEQ ID No:18 or part of these of the sequence listing as a probe. More specifically, there mentioned DNAs can be identified by carrying out the hybridization using filter with the colony or plaque-derived DNA immobilized thereon, at 65° C. in the presence of 0.7-1.0 M NaCl, and the washing the filter with 0.1 to 2×SSC at 65° C. (1-fold concentrated SSC solution comprising 150 mM NaCl and 15 mM sodium citrate). The hybridization can be carried out to the method described in Molecular cloning, A laboratory manual, second edition (Cold Spring Harbor Laboratory Press, 1989) or elsewhere.

In practice, the enantioselective enzymatic reduction may be performed using an oxidoreductase enzyme in suspension in the reaction mixture, or immobilized in a conventional manner. The enzyme may be utilized in a completely purified state, in a partially purified state, or in microbial cells where it was expressed. The cells themselves may be in a native state, a permeabilized state or a lysed state. It will be appreciated by those of ordinary skill in the art that use of the enzyme in the cells is preferred for the practice of the process of the invention since it represents a significant savings in cost. Most preferably, the enzyme is expressed in *E. coli* and used as a suspension of native cells.

The process of enzymatic reduction of compounds of formula (II) or (II') can be performed in a reaction mixture comprising said compound of formula (II) or (II'), an oxidoreductase, NADH or NADPH as a cofactor, a cosubstrate, such as a secondary alcohol and a suitable buffer.

The enantiomeric excess of the compound of formula (I) or (I') formed in the enantioselective enzymatic is at least about 90%, preferably at least about 95% and most preferably at least about 99%.

Derivatives of the oxidoreductase enzymes are those polypeptides having at least 60 (sixty) percent identity with the SEQ IDs given above and possessing oxidoreductase activity. Those skilled in the art are aware that there are systems and technology available to accurately determine sequence identity.

To determine the percent identity of two polypeptides, the sequences are aligned for optimal comparison purposes (e.g., gaps can be introduced in the sequence of a first amino acid sequence for optimal alignment with a second amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=# of identical positions/total # of positions (e.g., overlapping positions×100).

Based on the above general principles, the "percent identity" of two amino acid sequences is determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into the BLAST program of Altschul et al. (J. Mol. Biol. 215:403-410, 1990). When utilizing BLAST and Gapped BLAST programs, the default parameters of the respective programs are used.

The reduction reaction may be carried out in a single phase system having the cells containing the enzyme suspended therein. Alternatively, the reaction may be performed in a two-phase aqueous/organic solvent system as described in US 2009/0017510 and U.S. Pat. No. 7,371,903. The reaction may be carried out as a conventional batch reaction, or as a continuous process. It will be appreciated that one of the significant advantages of the enantioselective enzymatic reduction for commercial applications is that it is amenable to continuous operation.

The reaction mixture preferably contains from about 35 g to 500 g of cells per kg of raw product produced by the reduction. The suspension is the aqueous portion of the reaction mixture which also contains a buffer, for example a TEA (triethanolamine), phosphate, Tris/HCl or glycine buffer. The buffer may additionally comprise ions for the stabilization of the enzyme, for example, a source of magnesium ions. Additional additives that may be present in the buffer for stabilizing the enzymes may include a polyol, such as glycerol, sorbitols and the like, sulfur compounds, such as 1,4-DL-dithiothreitol, glutathione, cysteine or the like, amino acids and peptides, or detergents, such as DMSO. A preferred stabilizer for the enzyme is a polyol, particularly glycerol, which may be present in from about 10 to 80 percent, preferably about 50% by weight based on the weight of the cell suspension.

The enantioselective enzymatic reduction process is carried out using a coupled substrate principle wherein the reaction mixture utilizes a cosubstrate for the regeneration of the cofactor, or coenzyme, which functions to provide hydrogen for the reduction of the substrate of formula (II) or (II').

The cofactor preferably is utilized in the reduced state, i.e. NADPH or NADH, respectively. The cofactor is present in the reaction mixture in a concentration of from about 0.01 mM to 5 mM, preferably 0.05 mM to 0.5 mM.

In the reaction, the cosubstrate functions by being oxidized in the regeneration of the NADPH or NADH cofactor. The cosubstrate is present in the reaction mixture in from about 10% to 80% by volume, preferably from about 10% to 50% by volume, most preferably about 15-25% by volume.

The oxidized cofactor formed during the reduction of the compound of formula (II) or (II') is regenerated by oxidation of the cosubstate, which also can be catalyzed by the oxidoreductase enzyme. Thus, a particular economic advantage of the present process is that the oxidoreductase enzyme affects both reduction of the compound of formula (II) or (II') and oxidation of the cosubstrate, therefore no further enzyme has to be used for cofactor regeneration.

However, it is also within the scope of the present invention to add another enzyme to the reaction mixture for cofactor regeneration in order to enhance the rate of reduction of the substrate of formula (II) or (II').

In a further embodiment, an organic solvent that is not involved in the regeneration of the cofactor may be added to the reaction mixture and the reduction process performed in aqueous organic 2-phase system. Examples of such solvents include, without intended limitation, diethyl ether, tertiary butyl methyl ether, diisopropyl ether, dibutyl ether, ethyl acetate, butyl acetate, heptane, hexane or cyclohexane. Such a solvent may be present in from about 1% to 50% by volume based on the volume of the reaction mixture.

The amount of the substrate of formula (II) or (II') in the reaction mixture is preferably greater than about 0.1% by weight and may be increased to about 50% by weight, with a preferred concentration being from about 5 to 30% by weight.

The amount of said substrate will vary depending on the purity thereof since the process may be carried out with the substrate in a purified state or as raw product containing varying amounts and types of impurities.

The pH of the reaction mixture after the addition of all components will be in the range of 5 to 10, preferably from 7 to 9, and optimally about pH 7.5.

The enzymatic reduction according to the present invention is carried out at a temperature of from about 10-45° C., preferably from about 20-40° C., most preferably from about 25-35° C.

The enantioselective reduction process is cost-effective and environment-friendly in addition to providing the compounds of formula (I) or (I') in high yield and very high enantioselectivity. Thus, a compound of formula (I) or (I') of high optical purity can be obtained in the presence of the enzyme under the above-mentioned reaction conditions within from about 2 to 96 hours, preferably from about 4 to 24 hours.

During the incubation, the pH of the mixture is maintained within the ranges given above by periodic testing and the addition of a conventional acidic or basic reagent, for example sodium carbonate and sodium hydroxide, respectively.

EXPERIMENTAL SECTION

Example 1

Preparation of Enzyme Solution

Competent *Escherichia coli* StarBL21 (De3) cells (Invitrogen) or RB791 cells (*E. coli* genetic stock, Yale, USA), respectively, were transformed with the expression constructs pET21-MIX coding for the different oxidoreductases. The *Escherichia coli* colonies transformed with the expression constructs were then cultivated in 200 ml of LB medium (1% tryptone, 0.5% yeast extract and, 1% NaCl) with 50 μg/ml of ampicillin or 40 μg/ml of kanamycine, respectively, until an optical density of 0.5, measured at 550 nm, was reached. The expression of recombinant protein was induced by adding isopropylthiogalactoside (IPTG) with a concentration of 0.1 mM. After 16 hours of induction at 25° C. and 220 rpm, the cells were harvested and frozen at −20° C.

For preparation of the enzyme solutions, 30 g of cells were resuspended in 150 ml of triethanolamine buffer (100 mM, pH 7, 2 mM MgCl2, 10% glycerol) and homogenized using high pressure homogenizer. Subsequently, the enzyme solution was mixed with 150 ml glycerol and stored at −20° C.

Example 2

Preparation of the Reaction Mixture

Reaction mixtures were carried out using reduced cofactors (A) and using oxidized cofactor in combination with suitable cosubstrate for regeneration of reduced cofactor (B).

Depending on specific requirements of the individual enzyme either potassium phosphate 100 mM pH=7.5 or triethanolamine buffer 100 mM pH=7.5 were used. In addition the buffer can contain 1 mM MgCl$_2$ or 10% (v/V) for stabilization.

Reaction A
160 μl buffer
100 μl NADH/NADPH (40 mg/ml)
20 μl 2-Propanol
50 μl enzyme solution according to Example 1
2 mg Tert-butyl 3-oxopiperidinecarboxylate
Reaction B (with 2-Propanol)
450 μl buffer
0.05 mg NAD/NADP
50 μl enzyme solution according to Example 1
10 mg Tert-butyl 3-oxopiperidinecarboxylate
50 μl 2-Propanol
50 μl enzyme for regeneration if required
Reaction B (with 4-Methyl-2-Pentanol)
250 μl buffer
0.05 mg NAD/NADP
50 μl enzyme solution according to Example 1
10 mg Tert-butyl 3-oxopiperidinecarboxylate
250 μl 4-methyl-2-pentanol
50 μl enzyme for regeneration if required After 24 h incubation samples A and B were extracted with Dichloromethane and analyzed using GC. The samples were analyzed for enantiomeric excess and conversion.

Example 3

Preparation of tert-butyl (3S)-3-hydroxypiperidinecarboxylate Using Oxidoreductase SEQ ID NO1

75 μl of an enzyme suspension according to Example 1 of SEQ ID NO1 were added to a mixture of 450 μl of a buffer (100 mM potassium phosphate, pH 7.5, 1 mM ZnCl$_2$), 50 mg Tert-butyl 3-oxopiperidinecarboxylate, 0.05 mg NAD and 50 μl 2-propanol. The reaction mixture was incubated at room temperature under constant thorough mixing. After 24 h the substrate was completely converted to the corresponding tert-butyl (3S)-3-hydroxypiperidinecarboxylate showing an enantiomeric excess of >99.8%.

Example 4

Preparation of tert-butyl (3S)-3-hydroxypiperidinecarboxylate Using Oxidoreductase SEQ ID NO2

43 μl of an enzyme suspension according to Example 1 of SEQ ID NO2 were added to a mixture of 400 μl of a buffer (100 mM triethanolamine, pH 7.5, 1 mM MgCl$_2$), 50 mg Tert-butyl 3-oxopiperidinecarboxylate, 0.05 mg NAD and 100 μl 2-butanol. The reaction mixture was incubated at room temperature under constant thorough mixing. After 24 h about 98% of the substrate were converted to the corresponding tert-butyl (3S)-3-hydroxypiperidinecarboxylate showing an enantiomeric excess of >99.8%

Example 5

Preparation of tert-butyl (3S)-3-hydroxypiperidinecarboxylate Using Oxidoreductase SEQ ID NO5

43 μl of an enzyme suspension according to Example 1 of SEQ ID NO5 were added to a mixture of 400 μl of a buffer (100 mM triethanolamine, pH 7.5, 1 mM MgCl$_2$), 50 mg Tert-butyl 3-oxopiperidinecarboxylate, 0.05 mg NAD and 100 μl 2-propanol. The reaction mixture was incubated at room temperature under constant thorough mixing. After 24 h about 98% of the substrate were converted to the corresponding tert-butyl (3S)-3-hydroxypiperidinecarboxylate showing an enantiomeric excess of >99.8%

Example 6

Preparation of tert-butyl (3S)-3-hydroxypiperidinecarboxylate Using Oxidoreductase SEQ ID NO8

100 μl of an enzyme suspension according to Example 1 of SEQ ID NO8 were added to a mixture of 250 μl of a buffer (100 mM potassium phosphate, pH 7.5, 1 mM ZnCl$_2$), 50 mg Tert-butyl 3-oxopiperidinecarboxylate, 0.05 mg NAD and 250 μl 4-methyl-2-pentanol. The reaction mixture was incubated at room temperature under constant thorough mixing. After 24 h about 98% of the substrate were converted to the corresponding tert-butyl (3S)-3-hydroxypiperidinecarboxylate showing an enantiomeric excess of >99.8%

Example 7

Preparation of tert-butyl (3S)-3-hydroxypiperidinecarboxylate Using Oxidoreductase SEQ ID NO9

30 μl of an enzyme suspension according to Example 1 of SEQ ID NO8 were added to a mixture of 400 μl of a buffer (100 mM potassium phosphate, pH 7.5, 1 mM MgCl$_2$), 100 mg Tert-butyl 3-oxopiperidinecarboxylate, 0.05 mg NAD and 100 μl 2-propanol. The reaction mixture was incubated at room temperature under constant thorough mixing. After 24 h about 95% of the substrate were converted to the corresponding tert-butyl (3S)-3-hydroxypiperidinecarboxylate showing an enantiomeric excess of >99.8%.

Example 8

Preparation of tert-butyl (3S)-3-hydroxypiperidinecarboxylate Using Oxidoreductase SEQ ID NO9

10 g of the substrate Tert-butyl 3-oxopiperidinecarboxylate were suspended in 20 ml 2-propanol. In a separate vessel 10 mg NAD were solved in 80 ml buffer (100 mM potassium phosphate, pH 7.5, 1 mM MgCl$_2$) and 5.7 ml enzyme solution SEQ ID NO9 as in Example 1. The 2-propanol/substrate mixture was added to buffer/enzyme mixture. The reaction mixture was incubated at 30° C. under constant thorough mixing. After 24 h about 95% of the substrate were converted to the corresponding tert-butyl (3S)-3-hydroxypiperidinecarboxylate showing an enantiomeric excess of >99.8%.

Results are reported in Table 1

TABLE 1

| SEQ ID NOs. | Conversion in reaction A | tert-butyl (3S)-3-hydroxy piperidinecarboxylate | tert-butyl (3R)-3-hydroxy piperidinecarboxylate | Cofactor |
| --- | --- | --- | --- | --- |
| SEQ ID NO: 1 | >99 | 99.8 | 0.2 | NADH |
| SEQ ID NO: 2 | >99 | >99.9 | n.d | NADH |
| SEQ ID NO: 3 | >99 | 99.5 | 0.5 | NADPH |
| SEQ ID NO: 4 | >99 | >99.9 | n.d | NADH |
| SEQ ID NO: 5 | >99 | >99.9 | n.d | NADPH |
| SEQ ID NO: 6 | >99 | >99.9 | n.d | NADH |
| SEQ ID NO: 7 | >99 | >99.9 | n.d | NADH |
| SEQ ID NO: 8 | >99 | >99.9 | n.d | NADH |
| SEQ ID NO: 9 | >99 | >99.9 | n.d | NADH |

| SEQ ID NOs | Conversion in reaction B | tert-butyl (3S)-3-hydroxy piperidinecarboxylate | tert-butyl (3R)-3-hydroxy piperidinecarboxylate | Cofactor | Coenzyme Regeneration applied |
| --- | --- | --- | --- | --- | --- |
| SEQ ID NO: 1 | >99 | 99.8 | 0.2 | NAD | Substrate coupled, 2-propanol |
| SEQ ID NO: 2 | >99 | >99.9 | n.d | NAD | Substrate coupled, 2-propanol |
| SEQ ID NO: 4 | >99 | >99.9 | n.d | NAD | Substrate coupled, 2-propanol |
| SEQ ID NO: 6 | >97 | >99.9 | n.d | NAD | Enzyme coupled, 2-Methyl-4-pentanol |
| SEQ ID NO: 7 | >99 | >99.9 | n.d | NAD | Substrate coupled, 2-propanol |
| SEQ ID NO: 8 | >97 | >99.9 | n.d | NAD | Enzyme coupled, 2-Methyl-4-pentanol |
| SEQ ID NO: 9 | >98 | >99.9 | n.d | NAD | Substrate coupled, 2-propanol |

The invention claimed is:

1. A process for the preparation of a compound of formula (I)

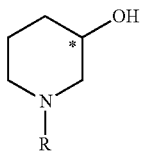

wherein the chiral carbon is in the (R) or in the (S) configuration;

R is selected from hydrogen and $COR_1$;

$R_1$ is selected from hydrogen, $C_1$-$C_6$-alkyl and $OR_2$;

$R_2$ is selected from $C_1$-$C_6$-alkyl and benzyl, said benzyl being optionally substituted by one or more $C_1$-$C_6$-alkyl groups;

said process comprising reducing a compound of formula (II)

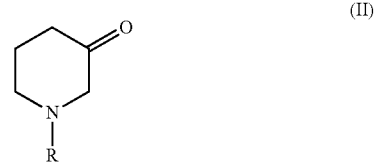

wherein R is defined as above, with an oxidoreductase of SEQ ID NO: 1 in the presence of a cofactor and of a cosubstrate regenerating said cofactor.

2. The process of claim 1, R is $COR_1$.

3. The process of claim 2, $R_1$ is $OR_2$.

4. The process of claim 3, wherein R is COOtBu.

5. The process of claim 3, wherein R is COObenzyl.

6. The process of claim 1, wherein said cofactor is selected from NADH and NAPDH.

7. The process of claim 1, wherein said cosubstrate is a secondary alcohol.

8. The process of claim 7, wherein said secondary alcohol is selected from 2-propanol, 2-butanol, 2-pentanol, 4-methyl-2-pentanol, 2-heptanol and 2-octanol.

* * * * *

SEQUENCE LISTING

<160> NUMBER OF SEQ ID NOS: 18

<210> SEQ ID NO 1
<211> LENGTH: 341
<212> TYPE: PRT
<213> ORGANISM: Pichia capsulata

<400> SEQUENCE: 1

Met Ser Ala Leu Ser Lys Thr Gln Ala Gly Tyr Ile Phe Lys Lys Gly
1               5                   10                  15

Ala Gly His Ile Val Lys Ala Glu Val Pro Ile Pro Lys Pro Thr Gly
            20                  25                  30

Ala Gln Ser Leu Leu Arg Val Lys Ala Ala Gly Met Cys His Ser Asp
        35                  40                  45

Leu His Val Ile Gly Glu Thr Leu Glu Val Pro Thr Asp Gly Tyr Val
50                  55                  60

Leu Gly His Glu Ile Ala Gly Glu Leu Val Glu Ile Gly Asp Ser Val
65                  70                  75                  80

Asn Pro Glu Val Phe Lys Val Gly Arg Tyr Ala Val His Gly Leu
                85                  90                  95

Asn Ser Cys Gly Ser Cys Glu Met Cys Arg Thr Gly His Asp Asn Asp
                100                 105                 110

Cys Thr Gly Asn Glu Ser Lys Trp Tyr Gly Leu Gly Ile Ser Gly Gly
            115                 120                 125

Tyr Gln Gln Tyr Leu Leu Val Pro Asn Ser His His Leu Leu Pro Ile
130                 135                 140

Pro Asp Asn Val Ser Tyr Glu Val Ala Ala Thr Ser Asp Ala Val
145                 150                 155                 160

Leu Thr Pro Tyr His Ala Ile Lys Asn Ser Gly Val Thr Pro Ser Ser
                165                 170                 175

Lys Val Leu Met Phe Gly Leu Gly Gly Leu Gly Ser Asn Ala Leu Gln
            180                 185                 190

Ile Leu Lys Ala Phe Gly Ala Tyr Val Val Ala Val Asp Val Lys Pro
            195                 200                 205

Ala Ser Lys Ala Ile Ala Asp Glu Phe Lys Ala Asp Glu Phe Tyr Thr
210                 215                 220

Asp Ile Ser Gln Ser Ser Trp Lys Pro Ala Ser Phe Asp Tyr Cys Phe
225                 230                 235                 240

Asp Phe Val Ser Leu Gln Val Thr Phe Asp Ile Cys Gln Lys Tyr Ile
                245                 250                 255

Lys Ser His Gly Thr Ile Phe Pro Val Gly Leu Gly Ser Ser Lys Leu
            260                 265                 270

Thr Phe Asp Leu Gly Asn Leu Ala Leu Arg Glu Val Lys Ile Val Gly
            275                 280                 285

Asn Phe Trp Gly Thr Ser Gln Glu Gln Ile Glu Ala Met Glu Leu Val
290                 295                 300

Ser Ser Gly Arg Val Lys Pro Gln Val His Thr Thr Glu Leu Glu Asn
305                 310                 315                 320

Leu Pro Glu Ser Leu Glu Lys Leu Glu Glu Gly Lys Ile Asn Gly Arg
                325                 330                 335

Leu Val Met Leu Pro
            340

<210> SEQ ID NO 2
<211> LENGTH: 348
<212> TYPE: PRT
<213> ORGANISM: Rhodococcus erythropolis

<400> SEQUENCE: 2

Met Lys Ala Ile Gln Tyr Thr Arg Ile Gly Ala Glu Pro Glu Leu Thr
1               5                   10                  15

Glu Ile Pro Lys Pro Glu Pro Gly Pro Gly Glu Val Leu Leu Glu Val
            20                  25                  30

Thr Ala Ala Gly Val Cys His Ser Asp Asp Phe Ile Met Ser Leu Pro

```
            35                  40                  45
Glu Glu Gln Tyr Thr Tyr Gly Leu Pro Leu Thr Leu Gly His Glu Gly
 50                  55                  60

Ala Gly Lys Val Ala Ala Val Gly Glu Gly Val Gly Leu Asp Ile
 65                  70                  75                  80

Gly Thr Asn Val Val Tyr Gly Pro Trp Cys Gly Asn Cys Trp
                 85                  90                  95

His Cys Ser Gln Gly Leu Glu Asn Tyr Cys Ser Arg Ala Gln Glu Leu
                100                 105                 110

Gly Ile Asn Pro Pro Gly Leu Gly Ala Pro Gly Ala Leu Ala Glu Phe
                115                 120                 125

Met Ile Val Asp Ser Pro Arg His Leu Val Pro Ile Gly Asp Leu Asp
    130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ser Tyr Ala Val
                165                 170                 175

Val Ile Gly Thr Gly Gly Leu Gly His Val Ala Ile Gln Leu Leu Arg
                180                 185                 190

His Leu Ser Ala Ala Thr Val Ile Ala Leu Asp Val Ser Ala Asp Lys
            195                 200                 205

Leu Glu Leu Ala Thr Lys Val Gly Ala His Glu Val Val Leu Ser Asp
    210                 215                 220

Lys Asp Ala Ala Glu Asn Val Arg Lys Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
                260                 265                 270

Asp Gly Gln Ala His Ala Lys Val Gly Phe Phe Gln Ser Pro Tyr Glu
            275                 280                 285

Ala Ser Val Thr Val Pro Tyr Trp Gly Ala Arg Asn Glu Leu Ile Glu
    290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
                325                 330                 335

Thr Leu Ser Gly Arg Ala Val Val Val Pro Gly Leu
            340                 345

<210> SEQ ID NO 3
<211> LENGTH: 338
<212> TYPE: PRT
<213> ORGANISM: Metschnikowia zobellii

<400> SEQUENCE: 3

Met Thr Thr Ser Val Phe Val Ser Gly Ala Thr Gly Phe Ile Ala Gln
  1               5                  10                  15

His Val Val Lys Leu Leu Leu Ser Lys Gly Tyr Asn Val Val Gly Ser
                 20                  25                  30

Val Arg Thr Ala Glu Lys Gly Lys Asn Leu Ala Lys Leu Phe Gly Thr
             35                  40                  45

Gly Ser Phe Thr Tyr Glu Val Val Pro Lys Leu Glu Ala Pro Gly Ala
 50                  55                  60
```

```
Phe Asp Glu Ala Leu Glu Lys His Pro Glu Val Ser Val Phe Leu His
 65                  70                  75                  80

Thr Ala Ser Pro Val Thr Phe Asp Val Lys Asp Ile Glu Lys Glu Leu
                 85                  90                  95

Leu Leu Pro Ala Val Glu Gly Thr Lys Asn Val Phe Ser Ala Ile Lys
            100                 105                 110

Ala His Gly Pro Gln Ile Lys Asn Val Val Thr Ser Ser Val Ala
        115                 120                 125

Ala Ala Leu Asp Pro Ala Arg Asn Leu Asp Pro Thr Phe Thr Val Asn
        130                 135                 140

Glu Asp Ser Trp Asn Pro Ile Ser Trp Glu Asp Ser Lys Gln Asn Ala
145                 150                 155                 160

Met Thr Gly Tyr Phe Gly Ser Lys Lys Phe Ala Glu Lys Ala Ala Trp
                165                 170                 175

Asp Phe Val Glu Ala Glu Lys Pro Asn Phe Leu Leu Asn Thr Val Leu
            180                 185                 190

Pro Val Tyr Val Phe Gly Pro Gln Ala Phe Asp Ser Glu Val Lys Gly
        195                 200                 205

Glu Leu Asn Tyr Ser Ala Glu Ile Ile Asn Lys Leu Leu Lys Leu Gly
        210                 215                 220

Pro Asn Asp Glu Val Pro Ser Gln Leu Gly Gly Phe Val Asp Val Arg
225                 230                 235                 240

Asp Val Ala Lys Ala His Leu Ala Ala Phe Glu Gly Gly Leu Ser Asn
                245                 250                 255

Gln Arg Leu Leu Leu Arg Thr Ala Ala Phe Asn Ala Gln Arg Val Leu
            260                 265                 270

Asp Ile Ile Asn Asn Lys Phe Val Asn Leu Arg Gly Gln Leu Pro Thr
        275                 280                 285

Gly Thr Pro Cys Lys Gly Glu Pro Glu Ser Thr Gly Ser Val Thr Asp
        290                 295                 300

Asn Ser Arg Thr Lys Lys Leu Leu Asn Phe Pro Ala Ile Asp Leu Glu
305                 310                 315                 320

Asn Cys Val Val Asp Ser Val Thr Gln Leu Met Lys Ser Gln Lys Lys
                325                 330                 335

Val Leu

<210> SEQ ID NO 4
<211> LENGTH: 336
<212> TYPE: PRT
<213> ORGANISM: Candida parapsilosis

<400> SEQUENCE: 4

Met Ser Ile Pro Ser Ser Gln Tyr Gly Phe Val Phe Asn Lys Gln Ser
  1               5                  10                  15

Gly Leu Asn Leu Arg Asn Asp Leu Pro Val His Lys Pro Lys Ala Gly
             20                  25                  30

Gln Leu Leu Leu Lys Val Asp Ala Val Gly Leu Cys His Ser Asp Leu
         35                  40                  45

His Val Ile Tyr Glu Gly Leu Asp Cys Gly Asp Asn Tyr Val Met Gly
     50                  55                  60

His Glu Ile Ala Gly Thr Val Ala Ala Val Gly Asp Val Ile Asn
 65                  70                  75                  80

Tyr Lys Val Gly Asp Arg Val Ala Cys Val Gly Pro Asn Gly Cys Gly
                 85                  90                  95
```

```
Gly Cys Lys Tyr Cys Arg Gly Ala Ile Asp Asn Val Cys Lys Asn Ala
                100                 105                 110

Phe Gly Asp Trp Phe Gly Leu Gly Tyr Asp Gly Gly Tyr Gln Gln Tyr
            115                 120                 125

Leu Leu Val Thr Arg Pro Arg Asn Leu Ser Arg Ile Pro Asp Asn Val
        130                 135                 140

Ser Ala Asp Val Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335

<210> SEQ ID NO 5
<211> LENGTH: 352
<212> TYPE: PRT
<213> ORGANISM: Thermoanaerobacter brockii

<400> SEQUENCE: 5

Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140
```

```
Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350

<210> SEQ ID NO 6
<211> LENGTH: 347
<212> TYPE: PRT
<213> ORGANISM: Microbacterium sp.

<400> SEQUENCE: 6

Met Lys Ala Leu Gln Tyr Thr Lys Ile Gly Ser His Pro Glu Val Val
1               5                   10                  15

Glu Ile Glu Lys Pro Ser Pro Gly Pro Gly Gln Val Leu Leu Lys Val
                20                  25                  30

Thr Ala Ala Gly Val Cys His Ser Asp Glu Phe Val Met Ser Leu Ser
            35                  40                  45

Glu Glu Gln Tyr Thr Ala Ala Gly Tyr Pro Leu Pro Leu Thr Leu Gly
        50                  55                  60

His Glu Gly Ala Gly Ile Val Glu Glu Leu Gly Glu Gly Val Glu His
65                  70                  75                  80

Leu Ser Val Gly Asp Ala Val Ala Val Tyr Gly Pro Trp Gly Cys Gly
                85                  90                  95

Arg Cys Arg Asn Cys Ala Gln Gly Lys Glu Asn Tyr Cys Thr Asn Ala
            100                 105                 110

Gln Ala Glu Gly Ile Met Pro Pro Gly Leu Gly Ala Pro Gly Ser Met
        115                 120                 125

Ala Glu Tyr Met Ile Val Asp Ser Ala Arg His Leu Val Pro Leu Gly
    130                 135                 140

Asp Leu Asp Pro Val Gln Asn Val Ser Leu Thr Asp Ala Gly Leu Thr
145                 150                 155                 160

Pro Tyr His Ala Val Lys Thr Ser Leu Pro Lys Leu Gly Ala Gly Thr
```

```
                        165                 170                 175
Thr Ala Val Val Ile Gly Thr Gly Gly Leu Gly His Val Ala Ile Gln
                180                 185                 190

Ile Leu Arg Ala Val Ser Ala Ala Thr Val Ile Ala Leu Asp Val Asn
            195                 200                 205

Asp Glu Lys Leu Ala Leu Ala Lys Glu Val Gly Ala His His Thr Val
        210                 215                 220

Met Ser Asp Gly Gly Ala Val Asp Ala Ile Arg Arg Leu Thr Asp Gly
225                 230                 235                 240

Leu Gly Ala Asn Ala Val Phe Asp Phe Val Gly Ala Asp Pro Thr Ile
                245                 250                 255

Ala Thr Ala Ile Gly Ala Ala Ala Leu Asp Ala Asp Ile Thr Ile Val
                260                 265                 270

Gly Ile Gly Gly Gly Thr Ala His Val Gly Phe Gly Thr Val Ala Tyr
            275                 280                 285

Asp Ala Ala Leu Arg Ile Pro Tyr Trp Gly Ser Arg Ser Glu Leu Ile
        290                 295                 300

Glu Val Leu Asp Leu Ala Arg Ser Gly Gln Val Gly Val Glu Ile Gln
305                 310                 315                 320

Arg Tyr Ser Leu Asp Asp Gly Pro Lys Ala Tyr Glu Ala Leu Ala Ala
                325                 330                 335

Gly Thr Val Arg Gly Arg Ala Val Ile Val Pro
            340                 345

<210> SEQ ID NO 7
<211> LENGTH: 346
<212> TYPE: PRT
<213> ORGANISM: Rhodococcus ruber

<400> SEQUENCE: 7

Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
                20                  25                  30

Thr Ala Ala Gly Leu Cys His Ser Asp Ile Phe Val Met Asp Met Pro
            35                  40                  45

Ala Glu Gln Tyr Ile Tyr Gly Leu Pro Leu Thr Leu Gly His Glu Gly
        50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190
```

Ala Val Ser Ala Ala Arg Val Ile Ala Val Asp Leu Asp Asp Arg
            195                 200                 205

Leu Ala Leu Ala Arg Glu Val Gly Ala Asp Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
                260                 265                 270

Ala Gly Ala His Ala Lys Val Gly Phe Phe Met Ile Pro Phe Gly Ala
            275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345

<210> SEQ ID NO 8
<211> LENGTH: 336
<212> TYPE: PRT
<213> ORGANISM: Pichia stipidis

<400> SEQUENCE: 8

Met Ser Ile Pro Ala Thr Gln Tyr Gly Phe Val Phe Thr Lys Lys Asp
1               5                   10                  15

Gly Leu Lys Ile Arg Glu Asn Met Pro Val Leu Glu Pro Lys Ala Asp
            20                  25                  30

Gln Val Leu Leu Lys Val Asp Ala Val Gly Leu Cys His Ser Asp Leu
        35                  40                  45

His Ala Ile Tyr Asp Gly Phe Asp Phe Gly Asp Asn Tyr Val Met Gly
    50                  55                  60

His Glu Ile Ala Gly Thr Ile Val Lys Lys Gly Ala Met Val Asp Phe
65                  70                  75                  80

Trp Asp Leu Asn Thr Arg Val Ala Cys Phe Gly Pro Asn Ser Cys Gly
                85                  90                  95

His Cys Gln Leu Cys Arg Thr Gly Phe Glu Asn Asp Cys Ile Asn Val
            100                 105                 110

Val Asn Gly Trp Phe Gly Leu Gly Lys Asn Gly Gly Tyr Gln Gln Tyr
        115                 120                 125

Leu Leu Val Glu Lys Pro Arg Asn Leu Val Ala Ile Pro Asp Asn Val
130                 135                 140

Glu Leu Ser Asp Ala Ala Ala Ile Thr Asp Ala Leu Leu Thr Pro Tyr
145                 150                 155                 160

His Ala Met Arg Leu Ala Gly Val Arg Ser Gly Thr Lys Leu Leu Gln
                165                 170                 175

Ile Gly Ala Gly Gly Leu Gly Val Asn Gly Ile Gln Ile Ala Lys Ala
            180                 185                 190

Phe Gly Ala Gln Val Thr Val Ile Asp Lys Lys Pro Glu Ala Val Asp
        195                 200                 205

Val Ala Lys Ser Leu Gly Ala Asp Glu Val Tyr Ser Ala Leu Pro Glu
210                 215                 220

```
Ser Thr Ser Pro Gly Ser Phe Asp Val Ala Ile Asp Tyr Val Ser Thr
225                 230                 235                 240

Gln Gly Thr Phe Asp Thr Cys Gln Lys Tyr Val Arg Ser Lys Gly Asn
                245                 250                 255

Ile Val Pro Val Gly Leu Ala Ala Pro Arg Ile Ser Phe Asn Leu Gly
            260                 265                 270

Asp Leu Ala Leu Arg Glu Ile Asn Val Leu Gly Ser Phe Trp Gly Thr
        275                 280                 285

Ser Ser Asp Leu Lys Glu Cys Phe Asp Leu Val Ser Lys Gly Lys Val
    290                 295                 300

Lys Pro Lys Val Thr Val Ala Pro Leu Lys Gln Leu Pro Glu Tyr Ile
305                 310                 315                 320

Val Lys Leu Gln Asn Ser Ala Tyr Glu Gly Arg Val Val Phe Lys Pro
                325                 330                 335

<210> SEQ ID NO 9
<211> LENGTH: 347
<212> TYPE: PRT
<213> ORGANISM: Gordona rubropertinctus

<400> SEQUENCE: 9

Met Lys Ala Ile Gln Ile Ile Gln Pro Gly Lys Pro Pro Glu Leu Arg
1               5                   10                  15

Glu Val Glu Lys Pro Thr Pro Arg Pro Gly Gln Val Leu Leu Lys Val
            20                  25                  30

Thr Ala Ala Gly Ala Cys His Ser Asp Asp Phe Val Leu Asn Leu Pro
        35                  40                  45

Glu Glu Gly Phe Pro Tyr Pro Leu Pro Met Thr Leu Gly His Glu Gly
    50                  55                  60

Ala Gly Val Val Ala Glu Val Gly Thr Gly Val Thr Gly Ile Ser Glu
65                  70                  75                  80

Gly Thr Ser Val Ala Val Tyr Gly Ala Trp Gly Cys Gly Val Cys His
                85                  90                  95

Phe Cys Ala Arg Gly Leu Glu Asn Tyr Cys Ser Arg Ala Gly Glu Leu
            100                 105                 110

Gly Ile Thr Pro Pro Gly Leu Gly Asn Pro Gly Ala Met Ala Glu Tyr
        115                 120                 125

Leu Leu Val Asp Asp Ala Arg His Leu Val Pro Leu Gly Asp Leu Asp
    130                 135                 140

Pro Val Ala Ala Val Pro Leu Thr Asp Ala Gly Leu Thr Pro Tyr His
145                 150                 155                 160

Ala Ile Lys Pro Ser Leu Pro Lys Leu Val Gly Gly Thr Thr Ala Val
                165                 170                 175

Val Ile Gly Ala Gly Gly Leu Gly His Val Gly Ile Gln Leu Leu Arg
            180                 185                 190

His Leu Thr Pro Ser Arg Val Ile Ala Leu Asp Val Ser Asp Asp Lys
        195                 200                 205

Leu Ala Phe Ala Arg Glu Val Gly Ala His Glu Val Val Leu Ser Asp
    210                 215                 220

Ala Asp Ala Val Ala Asn Val Arg Lys Ile Thr Gly Asn Asp Gly Ala
225                 230                 235                 240

Thr Ala Val Phe Asp Phe Val Gly Leu Gln Pro Thr Leu Asp Ile Ala
                245                 250                 255

Met Gly Val Val Gly Thr Met Gly Asp Val Val Ile Val Gly Ile Gly
```

```
                    260                 265                 270
Asp Met Val Ala Thr Ala Lys Val Gly Phe Phe Thr Gln Pro Tyr Glu
            275                 280                 285

Val Ser Val Arg Ala Pro Tyr Trp Gly Ala Arg Asp Glu Leu Ile Glu
        290                 295                 300

Val Leu Asp Leu Ala Arg Asp Gly Val Leu Glu Val Ala Val Glu Arg
305                 310                 315                 320

Phe Ser Leu Asp Asp Gly Val Glu Ala Tyr Arg Arg Leu Ala Ala Asn
                325                 330                 335

Asp Leu Arg Gly Arg Ala Val Val Val Pro Asp
            340                 345

<210> SEQ ID NO 10
<211> LENGTH: 1026
<212> TYPE: DNA
<213> ORGANISM: Pichia capsulata

<400> SEQUENCE: 10
atgtctgctc tctccaaaac ccaggccggt tacatcttca agaagggtgc cggtcacatc      60
gtcaaggccg aggttccaat ccccaagcca actggtgccc aatctcttct tagggtcaag     120
gctgcaggaa tgtgccactc tgacttgcac gtcattggag aaacattgga ggtccctacc     180
gatgggtacg tgctcggtca cgaaattgct ggtgaattgg tggagatcgg agactcggtc     240
aaccctgaag ttttttaaggt gggaggccgt tatgctgttc atggactgaa ttcgtgtgga     300
tcctgtgaga tgtgtcgtac cggtcatgac aatgactgta ctggaaatga atcgaaatgg     360
tacggtctgg gaattagtgg tggttaccag cagtacctgc tggtgccaaa ttcgcaccat     420
ctattgccta ttccagataa cgtgtcctac gaagttgctg ctgccacctc tgatgctgtc     480
ttgactccat accatgctat caagaattcc ggagtgactc catcttctaa ggtgttgatg     540
tttggtctgg gtggtttggg atcgaacgca cttcagatcc tcaaggcatt tggagcctat     600
gtggttgccg ttgatgtcaa gcccgcatcc aaagcaattg ccgacgaatt caaagcggat     660
gaattctata ccgatatcag ccaatcttct tggaaaccag cctcgtttga ttactgtttt     720
gacttcgttt cgctgcaggt caccttcgac atctgccaga agtatatcaa gtcccacggt     780
accatcttcc cagtgggtct gggctcgagc aagctgactt tcgacttggg aaacctggca     840
ttgcgtgaag taaaaattgt tggtaacttc tggggtactt ctcaggaaca gatcgaagca     900
atggagctgg ttagctcggg tagggtcaag cctcaagttc acaccaccga acttgaaaac     960
cttcctgaat cacttgaaaa actggaggag ggtaagatca tggaagatt ggttatgctt      1020 ccatga                                                                1026

<210> SEQ ID NO 11
<211> LENGTH: 1047
<212> TYPE: DNA
<213> ORGANISM: Rhodococcus erythropolis

<400> SEQUENCE: 11
atgaaggcaa tccagtacac gagaatcggc gcggaacccg aactcacgga gattcccaaa      60
cccgagcccg gtccaggtga agtgctcctg gaagtcaccg ctgccggcgt ctgccactcg     120
gacgacttca tcatgagcct gcccgaagag cagtacacct acggccttcc gctcacgctc     180
ggccacgaag gcgcaggcaa ggtcgccgcc gtcggcgagg gtgtcgaagg tctcgacatc     240
ggaaccaatg tcgtcgtcta cgggccttgg ggttgtggca actgttggca ctgctcacaa     300
```

```
ggactcgaga actattgctc tcgcgcccaa gaactcggaa tcaatcctcc cggtctcggt        360
gcacccggcg cgttggccga gttcatgatc gtcgattctc ctcgccacct tgtcccgatc        420
ggtgacctcg acccggtcaa gacggtgccg ctgaccgacg ccggtctgac gccgtatcac        480
gcgatcaagc gttctctgcc gaaacttcgc ggaggctcgt acgcggttgt cattggtacc        540
ggcgggctcg gccacgtcgc cattcagctc ctccgtcacc tctcggcggc aacggtcatc        600
gctttggacg tgagcgcgga caagctcgaa ctggcaacca aggtaggcgc tcacgaggtg        660
gttctgtcgg acaaggacgc ggccgagaac gttcgcaaga tcactggaag tcaaggcgcc        720
gcactggttc tcgacttcgt cggctaccag cccaccatcg acaccgcgat ggctgtcgcc        780
ggtgtcggat cagacgtcac gatcgtcggg atcggggacg ccaggccca cgccaaagtc         840 gggttcttcc aaagtcctta cgaggcttcg gtgacagttc cgtattgggg tgcccgcaac        900
gagttgatcg aattgatcga cctcgcccac gccggcatct tcgacatcgc ggtggagacc        960
ttcagtctcg acaacggtgc cgaagcgtat cgacgactgg ctgccggaac gctcagcggc        1020
cgtgcggttg tggtccctgg tctgtag                                            1047

<210> SEQ ID NO 12
<211> LENGTH: 1018
<212> TYPE: DNA
<213> ORGANISM: Metschnikowia zobellii

<400> SEQUENCE: 12
atgaccactt cagtctttgt ctctggtgcc accggcttca ttgcccagca cgtcgtcaaa        60
ctccttctct cgaaaggcta caacgtcgtt ggctccgtca gaaccgccga gaaaggcaag       120
aacctagcaa agctatttgg caccggctcc ttcacctacg aggtggtgcc caaactcgaa       180
gcgcctggtg ccttttgacga ggccttggaa aagcatccag aggtgtctgt gttttttgcac    240 acggcctcgc ccgtcacctt tgacgtcaag gacattgaga aagagttgct tctccccgcc      300
gtcgagggca ccaaaaacgt cttttagtgcc atcaaagccc acggcccgca gatcaaaaac     360
gtcgtggtga cgtcctctgt tgctgcggca ctcgatcccg ctagaaacct ggaccccacg      420
ttcactgtga atgaagactc ttggaaccca atctcgtggg aggactcgaa gcagaacgcc      480
atgaccgggt actttggctc caagaagttt gcagagaagg ccgcgtggga ttttgtggaa     540
gccgagaagc ccaactttct gttgaacacc gtgttgcccg tgtacgtctt tggcccccag      600
gcgtttgact ccgaggtcaa gggcgagctc aactactctg ccgaaatcat caacaagttg      660
ttgaagttgg acccaacgac gaagtgccct cgcaactgg ggggtttcgt cgacgtgaga       720
gacgtggcca aggctcactt ggccgcattc gagggcggac tctcgaacca gcgccttttg      780
cttagaacgg cagcgtttaa tgcgcaacgc gtgcttgaca taatcaacaa taagtttgtt      840
aacttgagag acagttgcc cactggaacg ccttgtaaag gcgagcctga aagcactggc       900
tctgtgacgg acaattcgag aaccaagaag ttattgaact tcccagccat cgacttggag      960
aactgtgtgg tggactcggt tacccagctc atgaagtccc agaagaaggt tttgtaag       1018

<210> SEQ ID NO 13
<211> LENGTH: 1011
<212> TYPE: DNA
<213> ORGANISM: Candida parapsilosis

<400> SEQUENCE: 13
atgtcaattc catcaagcca gtacggattc gtattcaata agcaatcagg acttaatctg        60
agaaatgatt tgcctgtcca caagcccaaa gcgggtcaat tgttgttgaa agttgatgct       120
```

```
gttggattgt gtcattctga tttacatgtc atttacgaag ggttggattg tggtgataat      180
tatgtcatgg gacatgaaat tgctggaact gttgctgctg tgggtgatga tgtcattaac      240
tacaaggttg gtgatcgtgt tgcctgtgtc ggacccaatg gatgtggtgg gtgcaagtat      300
tgtcgtggtg ccattgacaa tgtatgtaaa aacgcatttg gtgattggtt cggattgggg      360
tacgatggtg ggtatcaaca gtacttgttg gttactagac cacgtaactt gtctcgtatc      420
ccagataacg tatctgcaga cgtggctgcg gcttcaactg atgctgtatt gacaccatat      480
cacgcaatca agatggctca agtgtcacca acttcgaata tcttgcttat tggtgctggt      540
ggattgggtg gaaatgcaat tcaagttgcc aaggcatttg gtgcgaaagt tactgttttg      600
gacaaaaaaa aggaggctcg tgaccaagca agaagttgg gtgctgatgc agtttatgaa       660
acattgccag aatccatttc tcctggctct ttttcagcat gttttgattt tgtttcagtg      720
caagctacat ttgatgtatg tcaaaagtat gttgaaccaa agggtgtaat tatgcccgtg      780
ggactcggtc tcctaatttt atcgtttaat ttgggagatt tggcattgag agaaaattcga     840 atcttgggta gttttgggg aactactaat gatttggatg atgttttgaa attggttagt      900
gaaggtaaag ttaaacccgt tgtgagaagt gccaaattga aggaattgcc agagtatatt     960
gaaaaattga gaaacaatgc ttatgaaggt agagttgttt ttaatccata g              1011

<210> SEQ ID NO 14
<211> LENGTH: 1059
<212> TYPE: DNA
<213> ORGANISM: Thermoanaerobacter brockii

<400> SEQUENCE: 14
atgaaaggtt ttgcaatgct cagtatcggt aaagttggct ggattgagaa ggaaaagcct       60
gctcctggcc catttgatgc tatttgtaaga cctctagctg tggcccctg cacttcggac      120 attcataccg tttttgaagg cgccattggc gaaagacata acatgatact cggtcacgaa      180
gctgtaggtg aagtagttga agtaggtagt gaggtaaaag attttaaacc tggtgatcgc      240
gttgttgtgc cagctattac ccctgattgg cggacctctg aagtacaaag aggatatcac      300
cagcactccg gtggaatgct ggcaggctgg aaattttcga atgtaaaaga tggtgttttt     360
ggtgaatttt ttcatgtgaa tgatgctgat atgaatttag cacatctgcc taaagaaatt     420
ccattggaag ctgcagttat gattcccgat atgatgacca ctggttttca cggagctgaa     480
ctggcagata tagaattagg tgcgacggta gcagttttgg gtattggccc agtaggtctt     540
atggcagtcg ctggtgccaa attgcgtgga gccggaagaa ttattgccgt aggcagtaga    600
ccagtttgtg tagatgctgc aaaatactat ggagctactg atattgtaaa ctataaagat     660
ggtcctatcg aaagtcagat tatgaatcta actgaaggca aaggtgtcga tgctgccatc      720
atcgctggag gaaatgctga cattatggct acagcagtta gattgttaa acctggtggc       780 accatcgcta atgtaaatta ttttggcgaa ggagaggttt tgcctgttcc tcgtcttgaa     840
tggggttgcg gcatggctca taaaactata aaaggcgggc tatgccccgg tggacgtcta      900
agaatggaaa gactgattga ccttgttttt tataagcgtg tcgatccttc taagctcgtc     960
actcacgttt tccggggatt tgacaatatt gaaaagcct ttatgttgat gaaagacaaa      1020
ccaaaagacc taatcaaacc tgttgtaata ttagcataa                             1059

<210> SEQ ID NO 15
<211> LENGTH: 1044
<212> TYPE: DNA
```

<213> ORGANISM: Microbacterium sp.

<400> SEQUENCE: 15

```
atgaaggcac tccagtacac gaagatcgga tcccaccccg aagtcgtcga gatcgagaag      60
ccctcgccgg gtcccgggca ggtactgctc aaagtcaccg ccgccggcgt ctgccactcg     120
gacgagttcg tgatgagcct cagcgaggag cagtacaccg ctgccggcta ccccctgccg     180
ctcaccctcg gcacgaagg cgccggcatc gtcgaggagc tcggcgaagg tgtcgagcac     240
ctgagcgtcg agacgccgt cgccgtctac ggccctggg gttgcggccg ctgccgcaac     300
tgcgcgcagg gcaaggagaa ctactgcacg aacgcccagg cggagggat catgcctccc     360
ggtctcgggg ctcccggctc aatggcggag tacatgatcg tcgacagcgc gcgacacctc     420
gttccgctcg cgacctcga ccccgtgcag aacgtttcct tgacggatgc cggcctgacc     480
ccgtaccacg cggtcaagac gtcacttccg aagctgggcg ccggaacgac ggcggtcgtg     540
atcggcaccg ggggtctcgg acacgtcgcg attcagatcc tgcgggcggt gtcggccgcg     600
accgtgatcg cgttggacgt caacgacgag aaactcgcgc tggccaagga ggtcggcgcc     660
catcacaccg tcatgagcga cggcggcgcc gtcgacgcga ttcgccggct caccgacggt     720
ctgggcgcga acgccgtctt cgacttcgtc ggtgcggacc cgacgatcgc gacggcgata     780
ggagcagccg cgctcgacgc agacatcacg atcgtcggca tcggcggcgg aacggctcac     840
gtcggtttcg gcaccgtcgc ttatgacgcg gcgcttcgca tcccgtattg gggctcgcgc     900
agcgaactga tcgaggtgct cgacctcgcg cgctcagggc aggtgggagt cgagatccag     960
cgctactcac tcgacgacgg cccgaaggcg tacgaggcgc tcgccgcggg cacggtccgc    1020
ggccgcgccg tcatcgtccc ctga                                            1044
```

<210> SEQ ID NO 16
<211> LENGTH: 1041
<212> TYPE: DNA
<213> ORGANISM: Rhodococcus ruber

<400> SEQUENCE: 16

```
atgaaagccc tccagtacac cgagatcggc tccgagccgg tcgtcgtcga cgtccccacc      60
ccggcgcccg ggcggggtga gatcctgctg aaggtcaccg cggccggctt gtgccactcg     120
gacatcttcg tgatggacat gccggcagag cagtacatct acggtcttcc cctcaccctc     180
ggccacgagg gcgtcggcac cgtcgccgaa ctcggcgccg cgtcaccgg attcgagacg     240
ggggacgccg tcgccgtgta cgggccgtgg gggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgcgccacct cgtcccgatc     420
ggggacctcg accccgtcgc ggcggttccg ctcaccgacg cgggcctgac gccgtaccac     480
gcgatctcgc gggtcctgcc cctgctggga cccggctcga ccgcggtcgt catcggggtc     540
ggcggactcg ggcacgtcgg catccagatc ctgcgcgccc tcagcgcggc ccgcgtgatc     600
gccgtcgatc tcgacgacga ccgactcgcg ctcgcccgcg aggtcggcgc cgacgcggcg     660
gtgaagtcgg gcgccggggc ggcggacgcg atcgggagc tgaccggcgg tgagggcgcg     720
acggcggtgt tcgacttcgt cggcgcccag tcgacgatcg acacggcgca gcaggtggtc     780
gcgatcgacg gcacacatctc ggtggtcggc atccatgccg gcgcccacgc caaggtcggc     840
ttcttcatga tcccgttcgg cgcgtccgtc gtgacgccgt actggggcac gcggtccgag     900
ctgatggacg tcgtggacct ggcccgtgcc ggccggctcg acatccacac cgagacgttc    960
```

```
                                      -continued accctcgacg agggacccac ggcctaccgg cggctacgcg agggcagcat ccgcggccgc   1020
ggggtggtcg tcccgggctg a                                            1041

<210> SEQ ID NO 17
<211> LENGTH: 1011
<212> TYPE: DNA
<213> ORGANISM: Pichia stipidis

<400> SEQUENCE: 17
atgtctattc ctgctacaca atatggtttc gtcttcacca aaaaggacgg tttaaaaatt     60
cgcgagaaca tgcctgttct cgaacccaag gctgaccaag tcttgcttaa agtcgacgca    120
gtaggattgt gtcactctga ccttcatgcc atctacgacg gcttcgactt tggtgacaat    180
tacgttatgg gccacgaaat cgccggcacc attgtcaaga agggagccat ggtcgacttt    240
tgggacctaa acacccgtgt tgcctgtttt ggtccaaact cctgtggcca ttgtcaactt    300
tgtcgtactg gttttgaaaa tgattgtatc aatgtcgtca acggctggtt tggattaggt    360
aaaaacggag gctaccagca atatttgttg gttgaaaagc ctcgtaattt ggttgctatt    420
ccagacaacg tcgagctgtc cgatgcagct gccattaccg acgctttgtt gacccctac    480 catgccatga gattagctgg tgttagatca ggcacgaagc tcttgcaaat tggtgctgga    540
ggattgggag taaatggtat tcagattgct aaagcatttg gagctcaagt cactgttatc    600
gacaaaaagc ccgaggctgt agacgtcgct aagagcctag gcgcagatga agtatattct    660
gcacttcctg aatcaaccag tccgggaagt ttcgatgttg ctatcgacta cgtttctact    720
caaggcactt tcgacacttg tcaaaagtac gtcagatcta agggtaatat tgttcccgtt    780
ggattggccg ctccaagaat ttcgtttaac ttgggagatt tggcccttag agaaattaat    840
gtccttggta gcttctgggg tacatcatcc gacttgaagg aatgtttcga tttggtcagc    900
aagggcaaag tcaaacctaa ggtgactgtt gctccattga agcaattgcc tgaatacatt    960
gtcaagttac agaattcggc ctacgaaggt agagtcgtgt tcaagccatg a            1011

<210> SEQ ID NO 18
<211> LENGTH: 1044
<212> TYPE: DNA
<213> ORGANISM: Gordona rubropertinctus

<400> SEQUENCE: 18
atgaaggcca ttcagatcat ccagccgggc aaaccgccgg agctgcgcga ggtcgagaaa     60
cccacgccgc gtcccgggca ggtgttgctg aaggtgacgg cagccggcgc ctgccattcg    120
gacgacttcg tcctcaacct gcccgaggaa ggattcccct atcccttgcc gatgacgctc    180
ggccacgaag gggccggcgt ggtcgccgag gtcggtaccg gcgtcaccgg catctccgag    240
ggcacctcgg tggccgtgta cggagcctgg ggttgcggcg tctgtcactt ctgcgcccgc    300
ggcctggaga actactgcag ccgagccggc gaactcggca tcaccccacc gggtctcggc    360 aacccggggcg cgatggccga gtacctgctc gtggacgacg cacggcatct ggtgccgctc    420
ggtgacctcg acccggtggc tgcagtccca ctcaccgatg ccggcctcac gccctaccac    480
gcgatcaaac cctcgcttcc gaagctggtc ggcggcacca cggcagtggt catcggagcc    540
ggtggtctcg ggcatgtcgg gatccaactg cttcgccacc tgaccccgtc ccgggtgatc    600
gctctcgacg tgagcgacga caagctcgcg ttcgcgcgcg aggtcgggc tcacgaggtg    660 gtgctctccg acgccgatgc cgtcgcgaac gtccgcaaga tcaccggcaa cgatggtgcg    720
```

```
accgccgtct tcgacttcgt cgggctgcaa cctacgctcg acatcgcgat gggcgtcgtc    780
gggaccatgg gtgacgtggt gatcgtgggc atcggtgaca tggtcgccac ggcgaaggtc    840
ggcttcttca cccagcccta cgaggtgtcg gtacgcgcgc cgtactgggg ggcgcgcgac    900
gaactcatcg aggtgctgga tctcgcacgc gatggggttc tcgaggtggc ggtcgaacga    960
ttctcactcg atgacggcgt cgaggcctac cggcgactgg ccgccaatga ccttcgaggg   1020
cgagcagtcg tggtgcctga ctga                                         1044
```